US012083312B2

(12) United States Patent
Schwarz et al.

(10) Patent No.: US 12,083,312 B2
(45) Date of Patent: Sep. 10, 2024

(54) SUPPORTING / HOLDING DEVICE WITH AN INTELLIGENT COVER FOR MEDICAL FLUID PUMPS

(71) Applicant: B. Braun Melsungen AG, Melsungen (DE)

(72) Inventors: Jan Schwarz, Melsungen (DE); Peter Heine, Landsberied (DE); Sebastian Hoernig, Weichs (DE); Guenter Schmid, Germering (DE)

(73) Assignee: B. Braun Melsungen AG, Melsungen (DE)

( * ) Notice: Subject to any disclaimer, the term of this patent is extended or adjusted under 35 U.S.C. 154(b) by 58 days.

(21) Appl. No.: 17/849,831

(22) Filed: Jun. 27, 2022

(65) Prior Publication Data

US 2023/0001072 A1 Jan. 5, 2023

(30) Foreign Application Priority Data

Jul. 1, 2021 (DE) ...................... 20 2021 103 538.2

(51) Int. Cl.
*A61M 5/142* (2006.01)

(52) U.S. Cl.
CPC ....... *A61M 5/142* (2013.01); *A61M 2205/502* (2013.01); *A61M 2209/082* (2013.01)

(58) Field of Classification Search
CPC .. A61M 5/142; A61M 5/1413; A61M 5/1415; A61M 5/16831; A61M 2205/502; A61M 2205/505; A61M 2205/581; A61M 2205/583; A61M 2205/584; A61M 2205/18; A61M 2209/082; A61M 2209/084
See application file for complete search history.

(56) References Cited

U.S. PATENT DOCUMENTS

| | | | | |
|---|---|---|---|---|
| 4,898,578 A | * | 2/1990 | Rubalcaba, Jr. | ...... A61M 5/172 700/83 |
| 6,407,335 B1 | * | 6/2002 | Franklin-Lees | ........ F16M 13/02 174/58 |
| 7,884,735 B2 | * | 2/2011 | Newkirk | ................ A61G 7/012 5/512 |
| 9,808,316 B2 | * | 11/2017 | Hasegawa | ........... A61M 5/1413 |

(Continued)

FOREIGN PATENT DOCUMENTS

| | | |
|---|---|---|
| DE | 4030368 C1 | 11/1991 |
| DE | 102017122044 A1 | 3/2019 |

(Continued)

OTHER PUBLICATIONS

Search Report received in German Application No. 20 2021 103 538.2 dated Jun. 7, 2022, with translation, 5 pages.

*Primary Examiner* — Patrick D Hawn
(74) *Attorney, Agent, or Firm* — Christopher A. Rothe; Culhane PLLC

(57) ABSTRACT

A supporting or holding device for the position-safe holding of one or more medical fluid pumps during operation. The supporting or holding device has a basic body and a plurality of vertically spaced trays that project from a front side of the basic body. Each vertically spaced tray is adapted to receive a medical fluid pump. The supporting or holding device includes, at an uppermost end, an intelligent cover for the centralized representation of alarm(s) of the one or more medical fluid pumps.

18 Claims, 4 Drawing Sheets

(56) References Cited

U.S. PATENT DOCUMENTS

| | | | |
|---|---|---|---|
| D810,958 S * | 2/2018 | Lacy | D24/227 |
| 9,987,415 B2 * | 6/2018 | Asama | A61M 5/1417 |
| 10,232,108 B2 * | 3/2019 | Qi | A61M 5/172 |
| 11,217,340 B2 * | 1/2022 | Desch | A61M 5/172 |
| D979,764 S * | 2/2023 | Bürger | D24/185 |
| D989,298 S * | 6/2023 | Slaby | D24/185 |
| 2007/0219495 A1 * | 9/2007 | Kato | A61M 5/16827 604/131 |
| 2013/0272773 A1 * | 10/2013 | Kamen | A61M 39/28 403/11 |
| 2014/0046296 A1 * | 2/2014 | Clarke | A61M 5/1456 604/152 |
| 2014/0259837 A1 * | 9/2014 | Belliveau | G16H 20/17 211/49.1 |
| 2014/0321096 A1 * | 10/2014 | Kajackas | A61G 12/00 361/807 |
| 2015/0157791 A1 * | 6/2015 | Desch | G16H 20/17 702/50 |
| 2015/0196192 A1 * | 7/2015 | Kan | F16M 11/42 211/85.13 |
| 2019/0111209 A1 | 4/2019 | Murphy, Jr. et al. | |
| 2020/0129691 A1 * | 4/2020 | Lacy | A61M 5/16831 |
| 2021/0358589 A1 | 11/2021 | Mooney et al. | |
| 2022/0209461 A1 * | 6/2022 | Nielan | H01R 13/5219 |
| 2022/0384024 A1 * | 12/2022 | Artarit | G16H 40/63 |
| 2023/0200925 A1 * | 6/2023 | Bouchard | A61B 50/26 206/349 |

FOREIGN PATENT DOCUMENTS

| | | | | |
|---|---|---|---|---|
| DE | 202021103555 U1 * | 8/2021 | | A61M 5/1415 |
| ES | 2663270 T3 * | 4/2018 | | A61M 1/0031 |
| WO | WO-2015127189 A1 * | 8/2015 | | A61M 5/1408 |

* cited by examiner

SUPPORTING / HOLDING DEVICE WITH AN INTELLIGENT COVER FOR MEDICAL FLUID PUMPS

CROSS-REFERENCE TO RELATED APPLICATION

This application claims priority under 35 U.S.C. § 119 to German Application No. 20 2021 103 538.2, filed Jul. 1, 2021, the content of which is incorporated by reference herein in its entirety.

FIELD

The disclosure relates to a supporting or holding device with an intelligent cover for medical fluid pumps.

BACKGROUND

The development in modern medicine, especially in intensive-care medicine, has led to infusion therapies requiring the specific use and the exact dosing of highly efficient drugs. In the scope of these therapies, depending on the clinical picture, often a plurality of drugs and optionally parenteral feeding must be administered. Thus, there is a need of modular infusion devices adapted to be easily equipped with a plurality of fluid pumps/infusion pumps. For this purpose it is common to arrange the infusion pumps as a group during use in or at or by means of a supporting or holding device so as to ensure an intended operation and an intended use of the pumps.

A supporting and/or holding device for the position-safe holding of at least one medical fluid pump during its operation is, for instance, known from DE 10 2017 122 044 A1. This device comprises at least one plug-in position for holding the respective medical fluid pump which is provided with a guiding structure cooperating with the fluid pump when it is conveyed from a distal position to the proximal operating position. For this purpose, a plurality of vertically spaced trays adapted for receiving the at least one medical fluid pump project at the front side of the basic body of the supporting and/or holding device.

Furthermore, DE 40 30 368 C1 discloses modular infusion devices comprising a plurality of infusion pumps. The infusion device comprises a joint device holder at which numerous infusion devices/infusion pumps are fastened. The device holder comprises a column against which U-shaped housings of the infusion devices are pushed. Supporting elements as pushing guides for the housings and coupling elements which are connected with corresponding counterparts of the housings are provided at the column.

Conventionally, each of the medical fluid pumps comprises a display individually indicating an error occurring. In the case of a simultaneous operation of a plurality of these medical fluid pumps, especially if they are fastened in a plurality of supporting and/or holding devices, this individual display of errors may easily become confusing for the operator.

SUMMARY

It is therefore an object of the present disclosure to avoid or at least mitigate the afore-described disadvantages. For this purpose, a supporting/holding or arranging device for medical fluid pumps is to be provided which, during the operation of a number of (fluid) pumps, ensures a clear display of errors which is easy to perceive visually.

The disclosure accordingly relates to a supporting/arranging or holding device for the (position-safe) holding/fixing of at least one medical fluid pump/infusion pump during its operation with a basic body, from the front side of which a number of vertically/perpendicularly spaced trays project which are adapted to receive a medical fluid pump. The supporting or holding device comprises, at the uppermost end, an intelligent cover/lid/top part for the centralized presentation and/or output of visual (and possibly also acoustic) alarms of said at least one medical fluid pump which currently has a malfunction.

In other words, trays of a supporting or holding device are designed such that one respective medical fluid pump can be mounted in a receiving space between two of these trays. The rear sides of the medical fluid pumps abut on the front side of the basic body of the supporting or holding device (possibly with little clearance). Due to the vertical arrangement of the rectangular and plate-shaped trays the fluid pumps mounted are also arranged and/or stacked vertically. At the upper end of the supporting or holding device an intelligent cover is mounted which is, in the case of a malfunction of the pump, responsible for the alarm representation of the medical fluid pumps mounted in the supporting and/or holding device. In a mounted state of the medical fluid pumps a voltage supply of the fluid pumps and simultaneously also a communication between the fluid pumps and the supporting or holding device and/or the intelligent cover takes place via connections at the supporting or holding device.

It is thus ensured that the operator keeps a good overview of the fluid pumps throughout the operating period thereof. Especially for the simultaneous operation of a plurality of these supporting or holding devices do the intelligent covers of the supporting or holding devices facilitate the representation and perceptibility of the pump alarms.

Preferably, the intelligent cover comprises a light strip/light band/fluorescent strip visually indicating an error of the medical fluid pump in the supporting or holding device which comprises the most critical error.

In other words, the intelligent cover of the supporting or holding device indicates the error and/or the occurrence of an error of a mounted/fixed fluid pump visually by means of a light strip. Preferably, also the error (the type of error) of the fluid pump which comprises the most critical error is indicated, i.e., the intelligent cover always represents the error of one single fluid pump in case one and/or a plurality of fluid pumps comprise an error. For the case that an error is detected in one and/or a plurality of fluid pumps of a fluid pump system, i.e., if the intelligent cover indicates a visual alarm, the origin of the error is perceivable at the displays of the individual fluid pumps.

The indicating of an error of one single fluid pump by means of a light strip in the intelligent cover reduces the complexity of the error indication and accordingly also the manufacturing effort and/or the manufacturing costs of the intelligent cover. Moreover, this visual error/alarm indication ensures that an error as well as the type of error in the fluid pump system is perceivable within a supporting or holding device. For the case that a plurality of supporting or holding devices are used simultaneously, the light strips of the intelligent covers indicate the status of the used and/or active fluid pumps in a clear manner without an individual examining of the individual fluid pumps being necessary.

In a further preferred aspect the light strip of the intelligent cover emits, depending on the degree of error of the medical fluid pump concerned, green light, yellow light, or red light.

In other words, the light strip of the intelligent cover is designed such that it emits light of different colors, especially green light, yellow light, and red light. By means of this allocation of the different light colors and/or color coding the light strip of the intelligent cover indicates the degree of error and/or the gravity of error of the fluid pump concerned. Green light indicates a precise operation of the mounted fluid pumps, yellow light indicates a noncritical error of at least one mounted fluid pump, and red, especially blinking, light indicates a critical error of at least one mounted fluid pump, i.e., at least one fluid pump within the supporting and/or holding device comprises an error causing an operating failure of this at least one fluid pump.

The use of this color coding of the light strip reduces the complexity of the intelligent cover additionally since no separate display for the error indication is required.

In a further preferred aspect the light strip of the intelligent cover is formed of a plurality of, especially three, LED plates oriented at an angle to each other.

In other words, the light strip of the intelligent cover is of multi-part, especially three-part, design. The light strip comprises, for instance, three plates at which a plurality of LEDs are arranged, and which are oriented at an angle to each other, preferably an angle between 179° and 135°, and perpendicular to a printed circuit board of the intelligent cover on which they are fastened.

The angles between the LED plates of the light strip effect an approximate arcuate shape with a convex light emission and thus achieve a slight dispersion of the emitted light, so that the visual error indication by the intelligent cover can not only be perceived at the front side of the supporting and/or holding device, but also from the side of the supporting and/or holding device.

Preferably, the LED plates of the intelligent cover emit light of the same brightness or of different brightness and are, possibly independently thereof, in a further preferred manner controllable and/or controlled separately.

In other words, the individual LED plates are preferably controlled separately by electronics in the intelligent cover. The electronics of the intelligent cover is preferably designed such that all three LED plates emit a light with the same brightness, so that a homogeneous illumination is achieved. In a further embodiment the LED plates and/or the controlling electronics are preferably designed such that each of the three LED plates emits light with an individual brightness, i.e. with a brightness not adapted to each other.

In a further preferred aspect the intelligent cover comprises a loudspeaker.

In accordance with the disclosure the loudspeaker of the intelligent cover serves to acoustically represent and/or express an occurring error of one and/or a plurality of fluid pumps in the supporting or holding device. Preferably, this loudspeaker is arranged at the front side of the intelligent cover and assumes the expression of the acoustic alarms of the mounted fluid pumps. Only in the case of a faulty impairment of the acoustic alarm representation by the intelligent cover does the intelligent cover return this acoustic representation to the individual fluid pumps.

In addition to the visual alarm the acoustic alarm serves to warn the operator in the case of a faulty behavior of a fluid pump without the operator observing the supporting or holding device including the mounted fluid pumps. Thus, early error detection by the operator is ensured, so that he or she may react quickly enough.

In a further preferred aspect the intelligent cover comprises a light sensor detecting the light emission/radiation of the light strip and, possibly independently thereof, switching the, especially visual, output of the alarm and/or the error to the individual medical fluid pumps if a faulty behavior of the light strip is detected.

In other words, a light sensor of the intelligent cover recognizes whether the output of an alarm by the light strip works faultlessly. As soon as no light or too weak light is detected by the light sensor although light should be output by the intelligent cover, i.e. as soon as a faulty behavior of the light strip is detected, the intelligent cover returns the entire object of error indication to the individual fluid pumps in the supporting or holding device. Accordingly, the visual alarm indication only takes place by means of the displays of the individual fluid pumps. A further function of the light sensor consists in that the visual alarm indication of the intelligent cover is adapted to the ambient brightness.

This ensures that an error occurring in the mounted fluid pump system is, also despite a faulty failure of the light strip at the intelligent cover, consistently indicated and represented acoustically. In other words, the light sensor is part of a fail safe mechanism of the supporting or holding device.

In a further preferred aspect the intelligent cover comprises a lateral operating unit in the form of a membrane keyboard.

In other words, the intelligent cover of the supporting or holding device preferably comprises a membrane keyboard comprising additional control buttons/control keys, for instance, an on/off button or buttons for loudspeaker control. Furthermore, the membrane keyboard is provided and adapted to represent information about the intelligent cover by means of additional status indications, preferably in the form of LEDs. The status indications, for instance, render information about the charging and/or discharging state of a rechargeable battery of the intelligent cover or about the state of the mains operation.

Implementing the operating unit of the intelligent cover in the form of a membrane keyboard keeps the manufacturing effort and hence the manufacturing costs low. Moreover, such membrane keyboard is insensitive to fluids occurring in an operation of the medical fluid pumps. In contrast, when using conventional keys it is easy for fluid to enter the interior of the intelligent cover, which leads to unintended damage of the cover.

In a further preferred aspect the intelligent cover comprises a battery for its own power supply.

In other words, a battery, especially a rechargeable battery, is provided within the intelligent cover. The battery is easy to remove from a battery compartment, especially from the underside of the intelligent cover, as soon as the cover has been lifted off the holding device. The intelligent cover is controllable via the integrated battery or is controlled by means of the battery. Furthermore, the communication within the supporting or holding device is controllable via this battery or is controlled by means of the battery.

By means of the battery the intelligent cover is capable of bridging interruptions of the mains operation, for instance, during mains failures or during a transport in emergency doctor's operation. In particular, the battery maintains the communication within the supporting or holding device, so that the supporting or holding device and/or the intelligent cover continuously obtains information from the mounted fluid pumps even in the case of such an interruption. The communication in the other direction, i.e. from the intelligent cover to the medical fluid pumps, also takes place continuously.

In a further preferred aspect the intelligent cover comprises a circumferential drip edge/drip groove/drip trace at the underside.

In other words, a drip edge is formed at the lower side of the housing of the intelligent cover, which is provided and adapted to specifically break dripping fluid, so that the fluid pumps positioned below the intelligent cover are protected from the dripping fluid. Moreover, no dripping fluid thus gets to the electrical connections which are positioned below the intelligent cover and by which the intelligent cover is connected with the basic body of the supporting or holding device. Preferably, the drip edge is arranged such that penetrating of the fluid into the battery compartment at the underside of the intelligent cover is prevented.

Furthermore, the disclosure relates to a supporting or holding system with an afore-described supporting or holding device and at least one medical fluid pump held in the supporting or holding system by means of the tray provided in operating position. The uppermost medical fluid pump is mounted between the tray provided for it and the intelligent cover.

The medical fluid pump positioned in the mounted state in the uppermost receiving space of the supporting or holding device is mounted between the intelligent cover and a tray of the supporting or holding device. This means that the intelligent cover projects above this medical pump which at the same time rests/abuts on a tray.

BRIEF DESCRIPTION OF THE DRAWING FIGURES

The subject matter disclosed will now be explained in detail by means of advantageous embodiments and with reference to the associated Figures. The Figures are merely of schematic nature and serve exclusively for the understanding of the disclosure. It is pointed out that the features of the individual embodiments are exchangeable and may occur in any combination.

DETAILED DESCRIPTION

In the following, the present disclosure and the advantageous embodiments will be described by means of the Figures.

Figure 1:
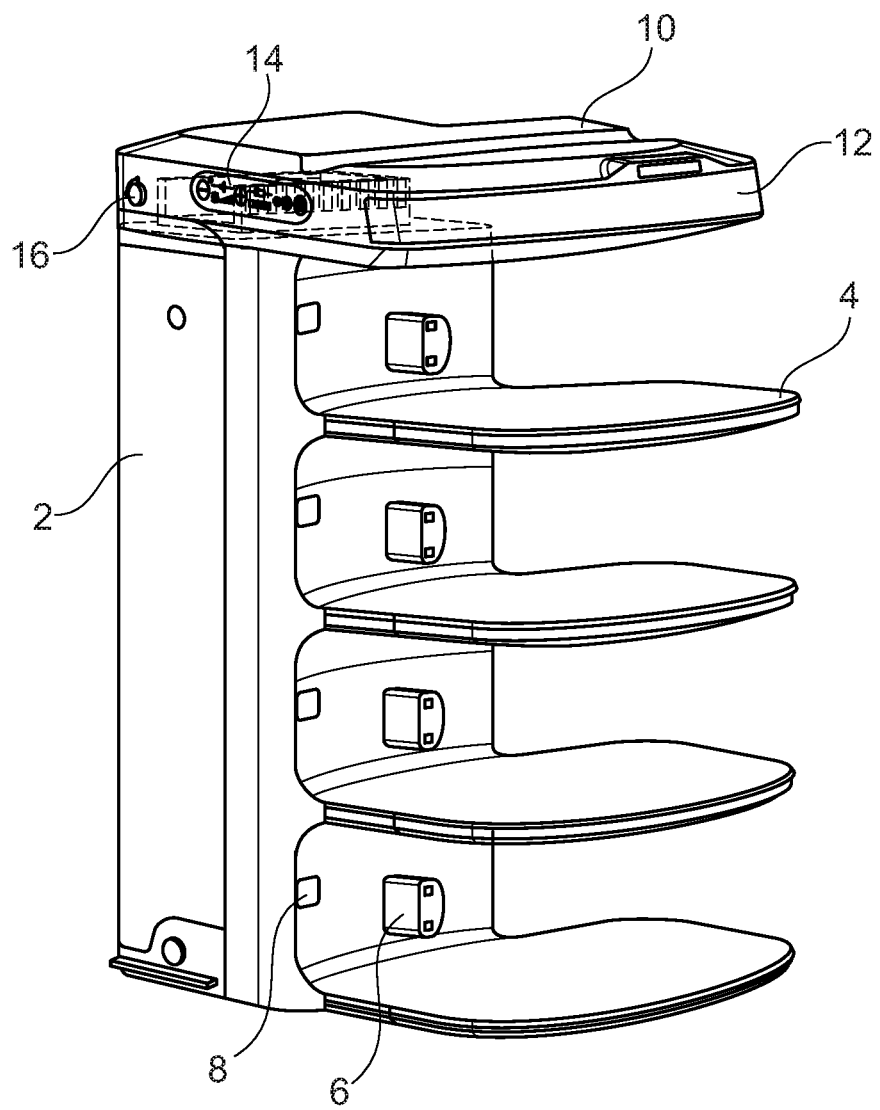
FIG. 1 is a front view of the supporting or holding device in accordance with the disclosure with a mounted intelligent cover.

FIG. 1 is a front view of the support/holding device 2 in accordance with the disclosure. The basic body of the support or holding device 2 is of elongate design and comprises a rectangular layout. At the front side of the support or holding device 2 four uniformly vertically spaced trays 4 are formed which are mounted perpendicular from the basic body. Four receiving spaces and/or slots for medical fluid pumps are formed between the trays 4. Each of the four receiving spaces comprises a centrally mounted mains plug 6 for the voltage supply of a medical fluid pump as well as an infrared interface 8 positioned at the left side of the fluid pump receptacle and serving as a communication interface between a medical fluid pump and the support or holding device 2. At the upper end of the support or holding device 2 an intelligent cover 10 is mounted which comprises a dark display strip 12 at the front side and at the left side face in front view a membrane keyboard 14 as an operating unit. The intelligent cover 10 projects above the basic body of the support or holding device 2, so that a medical fluid pump is receivable in the uppermost receiving space between the intelligent cover 10 and the uppermost tray 4. The intelligent cover 10 is firmly connected to the support or holding device 2 by means of a lateral yoke lock 16.

Figure 2:
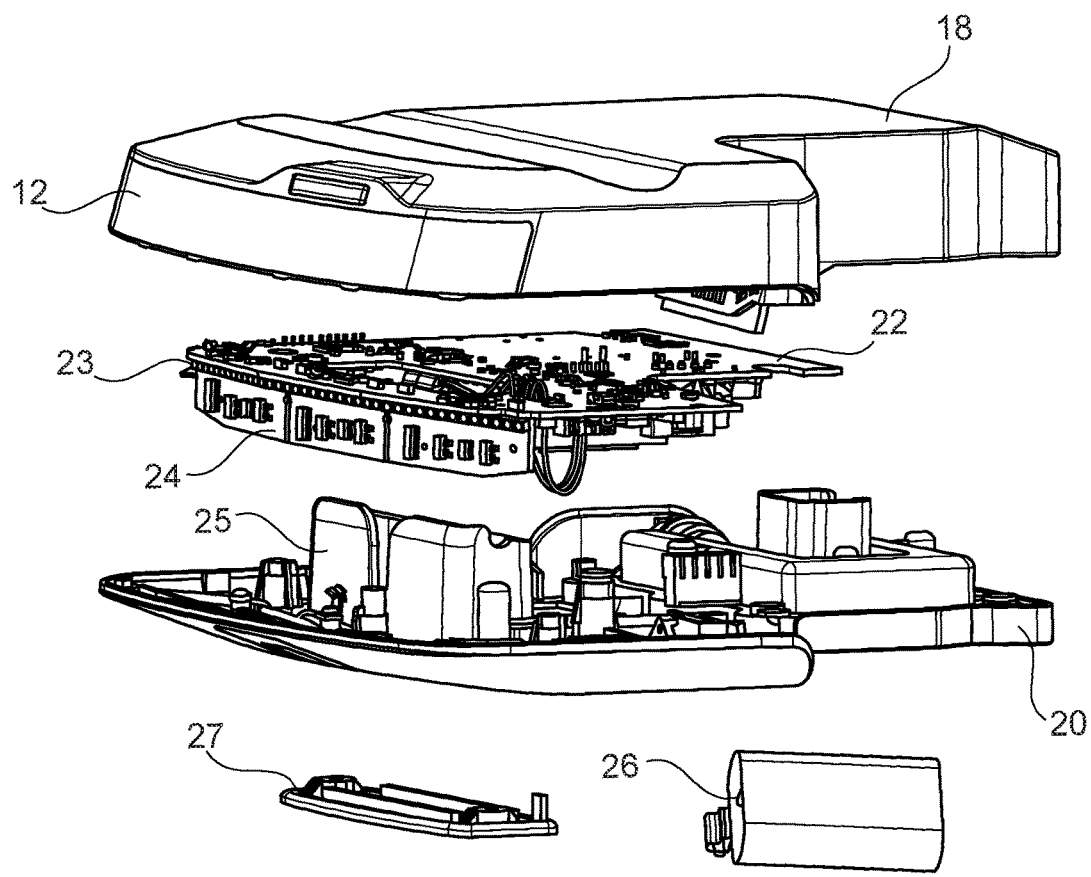
FIG. 2 is an exploded view of the intelligent cover of the supporting or holding device.

FIG. 2 is an exploded view of the intelligent cover 10 for illustrating the structure thereof. The intelligent cover 10 comprises a housing upper shell 18 and a housing lower shell 20 which receive a mainboard 22. A plurality of LEDs 23 are mounted to three serially arranged LED plates 24 which are oriented side by side in an arcuate shape and are in turn mounted substantially perpendicular at an end of the mainboard 22. The housing lower shell 20 comprises a battery compartment 25 for receiving a battery 26, wherein the battery compartment 25 is closable by a battery compartment lid 27 to the housing lower shell 20. Moreover, the housing lower shell 20 comprises the junction to the supporting or holding device 2. The housing upper shell 18 comprises at the front side a dark display strip 12 which extends completely through the front side of the cover 10 and projects moreover (in a bending manner) a bit into the side faces of the cover 10. The rear half of the intelligent cover 10 comprises a rectangular recess at the side opposing the membrane keyboard 14.

Figure 3:
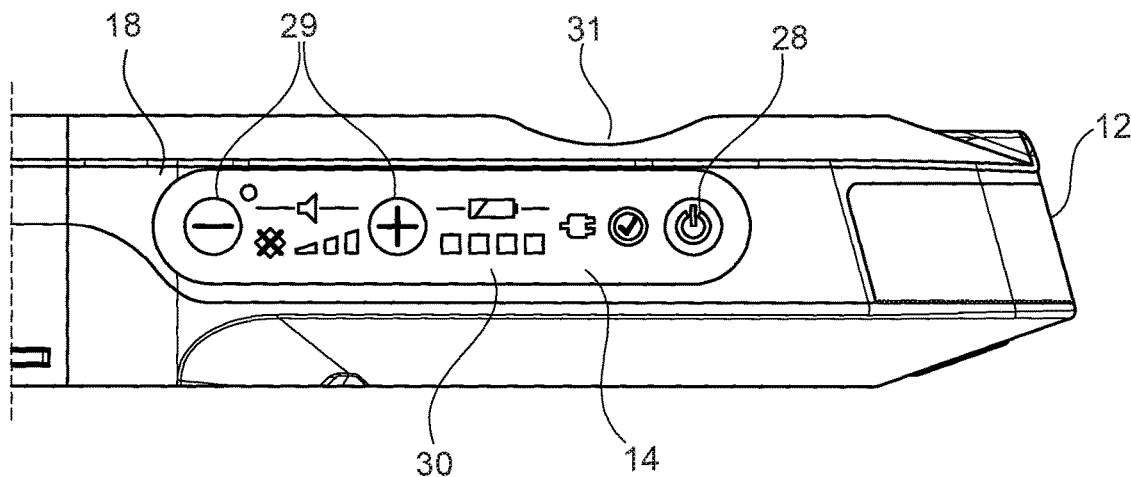
FIG. 3 is a side view of the intelligent cover of the supporting or holding device.

FIG. 3 is a side view of the intelligent cover which illustrates the lateral membrane keyboard 14 in a detailed manner. The display strip 12 which projects by bits into the side faces of the intelligent cover 10 is illustrated at the right in this representation. The membrane keyboard 14 is of stadium-shaped design and is mounted to the housing upper shell 18 of the intelligent cover 10. The membrane keyboard 14 comprises an on/off button 28 and two volume buttons 29 for increasing and/or reducing the acoustic alarm volume. Furthermore, the membrane keyboard 14 comprises information indicators 30, preferably LEDs, representing the status of the intelligent cover 10. For instance, the general system status of the cover, the battery charging state, the mains operation state, and the adjusted volume of the acoustic alarm are, for instance, indicated by the information indicators 30. At the upper side of the intelligent cover a depression 31 is provided which extends in parallel to the display strip 12 throughout the housing upper shell 18, and which works as a storage place of a syringe or of other medical instruments/equipment.

Figure 4:
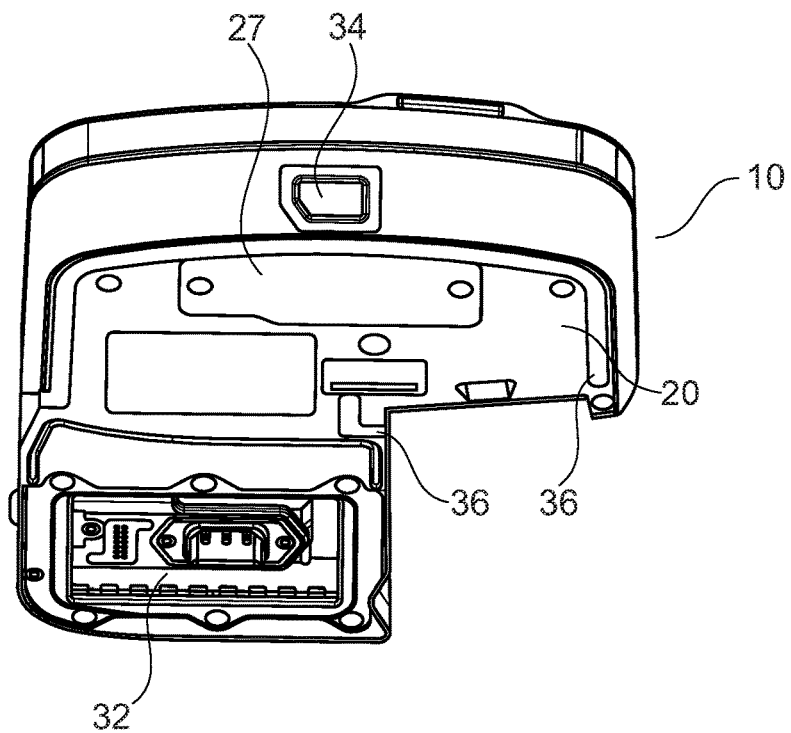
FIG. 4 is a representation of the underside of the housing of the intelligent cover of the supporting or holding device.

FIG. 4 is a representation of the underside of the intelligent cover 10. Here, the rectangular junction 32 for the supporting or holding device 2 is formed at the position farthest away from the front display strip 12. It comprises interfaces for the current flow as well as the information flow between the intelligent cover 10 and the supporting or holding device 2. A loudspeaker 34 is mounted in the front half at the underside of the cover 10. It is formed next to the display strip 12 of the front side centrally between the side faces of the cover 10. Adjacent to the loudspeaker 34 a drip edge 36 is formed at the underside of the housing, which extends in parallel to the display strip 12, past the battery compartment lid 27, and angles at both of the side faces of the cover housing, so that the drip edge 36 extends in these places in parallel along the side faces in the direction of the rear side, i.e., in the direction of the junction 32 of the cover. A second L-shaped drip edge 36 is formed relatively centrally next to the junction 32 of the housing lower shell 20.

Figure 5:
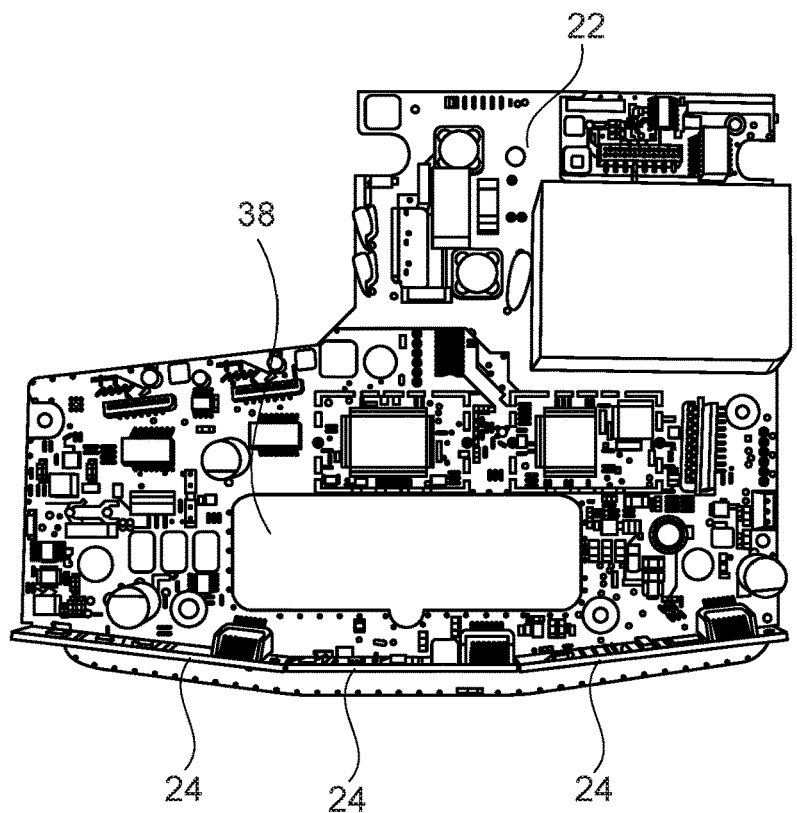
FIG. 5 is a top view of the underside of the mainboard of the intelligent cover of the supporting or holding device.

FIG. 5 is a top view of the underside of the mainboard 22 of the intelligent cover 10. The mainboard 22 comprises an almost rectangular recess corresponding to the recess of the cover housing. Moreover, the mainboard 22 comprises a central rectangular recess 38 through which the battery 26 mounted in the battery compartment 25 extends. FIG. 5 further shows electronic elements of the mainboard 22 and illustrates in particular the three LED plates 24 which are mounted substantially perpendicular to the mainboard 22 and which are placed next to each other and preferably slightly angled relative to each other. In this representation the three LED plates 24 project out of the image plane. Thus, light of the LED plates is irradiated both forward and also partially sideward of the holding device.

Figure 6:
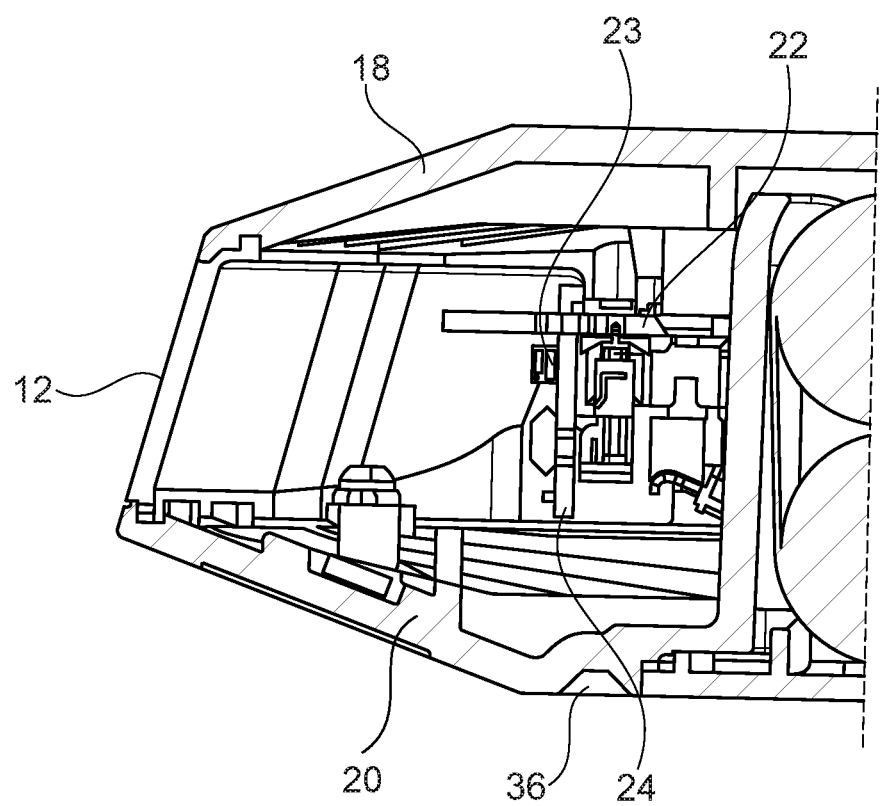
FIG. 6 is a sectional view through the front half of the intelligent cover of the supporting or holding device.

FIG. 6 is a sectional view with a sectional plane perpendicular through the display strip 12 and illustrates the front half of the intelligent cover 10. The horizontal faces of the housing upper shell 18 and of the housing lower shell 20 extend, from a certain distance to the display strip 12, in an angled manner toward same. The resulting inclination at the underside of the display strip 12 ensures that fluid is discharged along this inclination and flows into the afore-described drip edge 36. The drip edge 36 extends at the position forming the transition between the horizontal housing lower shell 20 and the inclination in the direction of the display strip 12. The intelligent cover 10 comprises a cavity behind the display strip 12 in which the mainboard 22 is screwed horizontally with the housing of the intelligent cover 10. The LED plate 24 which comprises the multi-colored LEDs 23 is fixed to the mainboard 22 perpendicular thereto and extends in the direction of the housing lower shell 20. The LEDs 23 are mounted to the upper end edge of the LED plates 24, i.e., at the end fixed with the mainboard 22. At the same time, the LED plates 24 are fixed to the mainboard 22 such that the mainboard 22 projects slightly over the LED plates 24 in the direction of the display strip 12, so that the light beam emitted by the LEDs 23 is restricted by the mainboard 22. Accordingly, only a small amount of light gets to the housing upper shell 18 and is focused more efficiently on the display strip 12.

The invention claimed is:

1. A supporting or holding device for the position-safe holding of at least one medical fluid pump during operation, the supporting or holding device having an uppermost end and comprising:
   a body having a front side;
   a plurality of vertically spaced trays projecting from the front side; and
   a cover at the uppermost end of the body, wherein the cover comprises a housing extending in a forward direction from the front side of the body, a display strip located at a foremost end of the housing and mounted to the housing to form an enclosure, and a plurality of lights mounted in the housing in a recess located behind the display strip, wherein the plurality of lights are configured to provide a centralized representation of alarms of the at least one medical fluid pump, each of the plurality of vertically spaced trays being configured to receive the at least one medical fluid pump.

2. The supporting or holding device according to claim 1, wherein the display strip is configured to indicate an error of the at least one medical fluid pump in the supporting or holding device which comprises a most critical error.

3. The supporting or holding device according to claim 2, wherein the display strip is configured to emit, depending on a degree of error of the at least one medical fluid pump, a green light, a red light, or a yellow light.

4. The supporting or holding device according to claim 1, wherein the plurality of lights are arranged on two or more LED plates angled with respect to each other.

5. The supporting or holding device according to claim 4, wherein the LED plates are configured to emit light of a same brightness or of different brightnesses and are controllable or controlled separately.

6. The supporting or holding device according to claim 2, wherein the cover comprises a light sensor configured to detect a light emission of the display strip and switch an output of an alarm to the at least one medical fluid pump when a faulty behavior of the display strip is detected.

7. The supporting or holding device according to claim 1, wherein the cover comprises a loudspeaker.

8. The supporting or holding device according to claim 1, wherein the cover comprises a lateral operating unit comprising a membrane keyboard.

9. The supporting or holding device according to claim 1 further comprising a battery that supplies power to the cover.

10. The supporting or holding device according to claim 1, wherein the cover comprises an underside with a circumferential drip edge comprising a groove extending into the underside.

11. A supporting or holding system comprising:
    a supporting or holding device according to claim 1; and
    a plurality of medical fluid pumps held in the supporting or holding system, each of the plurality of medical fluid pumps being held by one of the plurality of vertically spaced trays,
    the plurality of medical fluid pumps comprising an uppermost medical fluid pump,
    the uppermost medical fluid pump being mounted between one of the plurality of vertically spaced trays and the cover.

12. The supporting or holding device according to claim 4, wherein the plurality of lights are arranged on three LED plates angled with respect to each other.

13. The supporting or holding device according to claim 1, further comprising a mainboard extending generally horizontally within the housing.

14. The supporting or holding device according to claim 13, wherein the plurality of lights are mounted on plates extending generally vertically from the mainboard.

15. The supporting or holding device according to claim 14, wherein the display strip is secured to the housing with the plurality of lights spaced by a gap behind the display strip.

16. The supporting or holding device according to claim 1, wherein the housing comprises an underside that faces an uppermost one of the plurality of vertically spaced trays.

17. A supporting or holding device for the position-safe holding of at least one medical fluid pump during operation, the supporting or holding device having an uppermost end and comprising:
    a body having a front side;
    a plurality of vertically spaced trays projecting from the front side, wherein each of the plurality of vertically spaced trays is configured to receive the at least one medical fluid pump; and
    a cover at the uppermost end of the body, wherein the cover comprises a housing extending in a forward direction from the front side of the body, a display strip located at a foremost end of the housing, and a plurality of lights located inside the housing and behind the display strip, wherein the plurality of lights are configured to provide a centralized representation of alarms of the at least one medical fluid pump;

and a mainboard extending generally horizontally within the housing, wherein the plurality of lights are mounted on plates extending generally vertically from the mainboard.

18. A supporting or holding device for the position-safe holding of at least one medical fluid pump during operation, the supporting or holding device having an uppermost end and comprising:

a body having a front side;

a plurality of vertically spaced trays projecting from the front side, wherein each of the plurality of vertically spaced trays is configured to receive the at least one medical fluid pump; and a cover at the uppermost end of the body, wherein the cover comprises a housing extending in a forward direction from the front side of the body, a display strip located at a foremost end of the housing, and a plurality of lights located inside the housing and behind the display strip, wherein:

the plurality of lights are configured to provide a centralized representation of alarms of the at least one medical fluid pump, the display strip is configured to indicate an error of the at least one medical fluid pump in the supporting or holding device which comprises a most critical error, and the cover comprises a light sensor configured to detect a light emission of the display strip and switch an output of an alarm to the at least one medical fluid pump when a faulty behavior of the display strip is detected.

* * * * *